(12) United States Patent
Ranade (10) Patent No.: US 9,278,202 B2
(45) Date of Patent: Mar. 8, 2016

(54) APPARATUS FOR SENSING AND RESPONDING TO STRAIN IN AIRWAY DILATION SHAFT

(71) Applicant: Acclarent, Inc., Menlo Park, CA (US)

(72) Inventor: Shrirang V. Ranade, Foster City, CA (US)

(73) Assignee: Acclarent, Inc., Irvine, CA (US)

( * ) Notice: Subject to any disclaimer, the term of this patent is extended or adjusted under 35 U.S.C. 154(b) by 151 days.

(21) Appl. No.: 13/795,910

(22) Filed: Mar. 12, 2013

(65) Prior Publication Data
US 2014/0277060 A1  Sep. 18, 2014

(51) Int. Cl.
*A61M 29/00* (2006.01)
*A61M 29/02* (2006.01)
*A61M 25/01* (2006.01)
*A61M 25/00* (2006.01)
*A61M 25/10* (2013.01)

(52) U.S. Cl.
CPC ........... *A61M 29/02* (2013.01); *A61M 25/0102* (2013.01); *A61M 25/10184* (2013.11); *A61M 2025/0002* (2013.01); *A61M 2025/0008* (2013.01); *A61M 2025/1093* (2013.01); *A61M 2205/18* (2013.01); *A61M 2205/332* (2013.01); *A61M 2205/3344* (2013.01); *A61M 2205/581* (2013.01); *A61M 2205/582* (2013.01); *A61M 2205/583* (2013.01); *A61M 2210/1028* (2013.01); *A61M 2210/1032* (2013.01); *A61M 2210/1035* (2013.01)

(58) Field of Classification Search
CPC ...... A61M 29/02; A61M 25/10; A61M 16/80
USPC ......................... 606/192; 600/104; 604/96.01
See application file for complete search history.

(56) References Cited

U.S. PATENT DOCUMENTS

| | | | |
|---|---|---|---|
| 5,171,299 A | 12/1992 | Heitzmann et al. | |
| 8,448,636 B2 | 5/2013 | Singh | |
| 2009/0287118 A1* | 11/2009 | Malek | 600/585 |
| 2010/0113939 A1 | 5/2010 | Mashimo et al. | |
| 2010/0168511 A1* | 7/2010 | Muni et al. | 600/104 |

OTHER PUBLICATIONS

Non-Provisional U.S. Appl. No. 13/796,073, filed Mar. 12, 2013.
Non-Provisional U.S. Appl. No. 13/795,857, filed Mar. 12, 2013.

(Continued)

*Primary Examiner* — Victor Nguyen
(74) *Attorney, Agent, or Firm* — Frost Brown Todd LLC (57) ABSTRACT

An apparatus includes a balloon catheter, an inflatable balloon, and a force sensor. The balloon catheter is operable to communicate fluid to the balloon. The balloon is disposed on the distal end of the balloon catheter. The balloon is positionable within an airway or other anatomical passageway of a patient. The force sensor is positioned along the balloon catheter or in the balloon and is able to detect a physical change within the balloon catheter or balloon. A control logic may trigger a response based on readings by the force measuring device. For instance, the control logic may trigger an alert when a force related parameter exceeds a threshold; or when a rate of change in the parameter exceeds a threshold. In addition or in the alternative, the control logic may trigger a feature that is operable to reduce fluid pressure in the balloon in response to such conditions.

13 Claims, 4 Drawing Sheets

(56) References Cited

OTHER PUBLICATIONS

International Search Report dated May 27, 2014 for Application No. PCT/US2014/018037, 6 pages.

International Written Opinion dated May 27, 2014 for Application No. PCT/US2014/018037, 10 pages.

* cited by examiner

APPARATUS FOR SENSING AND RESPONDING TO STRAIN IN AIRWAY DILATION SHAFT

BACKGROUND

In some instances, it may be desirable to dilate an anatomical passageway in a patient. This may include dilation of ostia of paranasal sinuses, dilation of a patient's airway (e.g., to treat a stenosis within the larynx), dilation of the nasal cavity, dilation of the Eustachian tube, dilation of other passageways within the ear, nose, or throat, dilation of blood vessels, dilation of the urethra, etc. One method of dilating anatomical passageways includes using a guide wire and catheter to position an inflatable balloon within the anatomical passageway, then inflating the balloon with a fluid (e.g., saline) to dilate the anatomical passageway.

Airway stenosis (or "airway narrowing") is a medical condition that occurs when some portion of a patient's airway becomes narrowed or constricted, thus making breathing difficult. A stenosis may occur in any part of the airway including the larynx, trachea, bronchi, or a combination of any of the above mentioned regions. Both adults and children may develop a stenosis. In some instances, a stenosis is caused by intubation, which is when a tube is placed in the airway for ventilation/breathing assistance in a patent who cannot breathe. Intubation for prolonged periods of time may traumatize the airway, causing scar tissue formation that forms the stenosis.

Therapies for treating an airway stenosis range from endoscopic treatments, such as dilation and laser resection, to open procedures, such as laryngotracheal reconstruction. In one technique, a series of rigid dilators of increasing diameter are pushed down the airway, gradually expanding the constriction but also applying shear forces to the airway. Balloon catheters may also be used to perform dilation of an airway or other anatomical passageway. For instance, the expandable balloon may be positioned within a stenosis in an airway (e.g., larynx, trachea, bronchi, etc.) and then be inflated, to thereby dilate the airway and increase airflow. The dilated airway may then allow for improved breathing. An example of a system that may be used to perform such procedures is described in U.S. Pub. No. 2010/0168511, entitled "System and Method for Dilating an Airway Stenosis," published Jul. 1, 2010, the disclosure of which is incorporated by reference herein.

During the course of using a balloon dilation system such as the system described in U.S. Publication No. 2010/0168511, the user may wish to remove the system from the airway of the patient. Removing such a balloon system, if performed improperly, may expose the patient to physical risks. For example, if the user improperly attempts to remove a balloon system prior to fully deflating the balloon system, unwanted force may be applied to the airway and/or to the balloon system. In some instances of such improper use, the balloon may even become detached and become lodged in the airway, causing asphyxiation. In other instances, the user might improperly attempt to remove the balloon system with such force that the airway becomes strained in a harmful way.

While several airway dilation systems have been made and used, it is believed that no one prior to the inventor(s) has made or used the invention described in the appended claims.

BRIEF DESCRIPTION OF THE DRAWINGS

It is believed the present invention will be better understood from the following description of certain examples taken in conjunction with the accompanying drawings, in which like reference numerals identify the same elements and in which.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Balloon Dilation Catheter System

Figure 1:
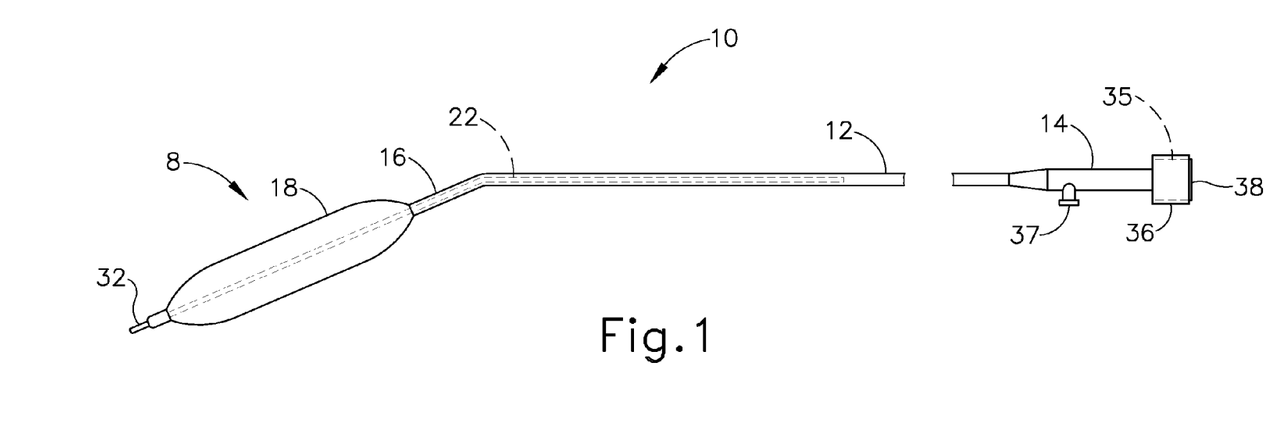
FIG. 1 depicts a side view of an exemplary system for dilating a stenosis in the airway, including a balloon catheter and a stylet.

FIG. 1 shows an exemplary dilation catheter system (8), which may be used to dilate a stenosis in an airway; or to dilate some other anatomical passageway (e.g., within the ear, nose, throat, cardiovascular system, etc.). At least part of system (8) may be constructed and operable in accordance with at least some of the teachings of U.S. Pub. No. 2010/0168511, the disclosure of which is incorporated by reference herein. It should be understood that dilation catheter system (8) may be used to dilate either a naturally occurring passageway in a patient or a surgically created passageway in a patient.

Dilation catheter system (8) of this example comprises a balloon catheter (10) and a stylet (22). Balloon catheter (10)

comprises a shaft (12) positioned between a hub (14) and a balloon (18). Balloon (18) is coupled to a distal end of shaft (12) and is configured to receive fluid through balloon catheter (10). Stylet (22) is slidably positioned through balloon catheter (10). In some versions, at least a portion of stylet (22) has a greater stiffness than at least a portion of balloon catheter (10), such that when stylet (22) is bent and inserted within balloon catheter (10), balloon catheter (10) at least partially conforms to the shape of stylet (22). In a dilation procedure, stylet (22) is used to advance balloon catheter (10) within an airway or targeted anatomical passageway (e.g., at a stenosis site). Balloon (18) may then be actuated to an expanded state to open or dilate the targeted anatomical passageway. Balloon (18) may then be actuated back to a collapsed state such that balloon (18) is deflated. This process may be repeated to dilate several anatomical passageways.

A. Exemplary Balloon Catheter

As shown in FIG. 1, balloon catheter (10) comprises a catheter shaft (12). An inflatable balloon (18) is attached to a distal end of shaft (12) via adhesive or other attachment means. A hub (14) is coupled to a proximal end of shaft (12) and comprises a stylet port (38) and an inflation port (37). Stylet (22) is inserted within stylet port (38) and generally resides within an inner lumen of shaft (12). Fluid (e.g., saline, etc.) is introduced through inflation port (37) through shaft (12) to inflate balloon (18).

Balloon catheter (10) may have any number of suitable sizes, shapes and configurations. For example, balloon (18) may have different lengths and diameters in different embodiments, to accommodate different patient anatomies. The overall catheter (10) length and diameter may also vary. For example, the overall length of balloon catheter (10) (i.e., from the proximal end of hub (14) to the distal end of catheter shaft (12)) is about 35-70 cm, such as less than or equal to about 50 cm, or about 45 cm.+−0.5 cm. Catheter (10) may be handled and manipulated with one hand. The working length of balloon (18) in FIG. 1 is about 40 mm+/−0.2 mm. By "working length" it is meant the length between the two tapered portions of balloon (18). In some versions, the working length of balloon (18) may range from between about 10 mm and about 60 mm such as about 16-45 mm. The outer diameter of the fully inflated working length of balloon (18) may also vary. In the present example, balloon (18) has an inflated diameter of about 14.1 mm+/−0.5 mm. In some versions, balloon (18) diameter may range from about 3 mm to about 24 mm, such as about 5-15 mm. A combination of balloon diameters and lengths may be provided, such that a physician may choose an appropriate size for an adult or pediatric patient. In one example, the following balloon diameters and lengths may be provided: 5 mm by 24 mm; 7 mm by 24 mm; 10 mm by 40 mm; and 14 mm by 40 mm. Of course, any of a number of other combinations of sizes of balloons (58) may be provided.

Any suitable material may be used to form balloon (18). Balloon (18) may be compliant, semi-compliant or non-compliant. Balloon (18) may be made of nylon, some other polymer, such as PTFE, and/or any other suitable material(s). In some versions, balloon (18) is formed of an elastic/extensible material that is resiliently biased to assume a shrunken, non-inflated configuration, such that the material forming balloon (18) is under increased tension when balloon (18) is in a non-deflated state. In some other versions, balloon (18) is formed of a material that is flexible yet substantially inelastic/non-extensible, such that the material forming balloon does not provide a significant resilient bias. In other words, balloon (18) does not stretch in response to increased fluid pressure inside balloon (18), even though the effective outer diameter of balloon (18) increases in response to increased fluid pressure. Such inelastic versions of balloon (18) may nevertheless be filled with fluid, with the fluid pressure being increased to provide an outwardly directed force via balloon (18), and this process may be referred to as "inflating." When the pressure of fluid inside balloon (18) is reduced, this process may be referred to as "deflating," even if the material forming balloon (18) does not elastically shrink, since balloon (18) may nevertheless flexibly collapse in response to reduced fluid pressure. Thus, it should be understood that the use of terms like "inflate," "inflated," "deflate," and "deflated" does not necessarily mean that the material forming balloon (18) undergoes any elastic stretching or shrinking as the fluid pressure within balloon (18) changes.

In some versions, balloon (18) may include an outer slip-resistant surface, which may be formed by a textured surface or a coating. Such a surface may help prevent slipping of balloon (18) out of an airway structure during inflation and/or may facilitate re-wrapping balloon (18) by hand after deflation if balloon (18) is to be used for a second or subsequent dilation procedure. Examples of such balloons are provided in U.S. patent application Ser. No. 13/796,073, entitled "Features to Enhance Grip of Balloon within Airway," filed on a date even herewith, published as U.S. Pub. No. 2014/0277071 on Sep. 18, 2014, the disclosure of which is incorporated by reference herein.

Catheter shaft (12) may also be formed of any suitable material. It may be desirable to form shaft (12) from material(s) selected so that shaft (12) is unlikely to kink when bent, such as when bent by stylet (22) and/or a user. One such material, for example, is Pebax, although other polymers may be used. Shaft (12) may also have any suitable color and may include one or more shaft markings. The shaft color and markings may be built into shaft (12) by using a colored material or may be added by applying paint or another colorant. In some versions, shaft (12) may have a dark color, such as black or dark blue, and one or more light colored markings may be applied over the dark shaft (12). In some versions, the markings (not shown) may include direct visualization markings (viewed directly with the naked eye or an endoscope) and/or radiographic markings (viewed with a radiographic device such as intraoperative fluoroscopy). Any suitable combination, size and color of markings may be used. One example of shaft color and shaft markings, which could be used or modified for balloon catheter (50), is the Relieva Solo Pro Sinus Balloon Catheter, manufactured by Acclarent, Inc. of Menlo Park, Calif.

B. Exemplary Stylet

Figure 2:
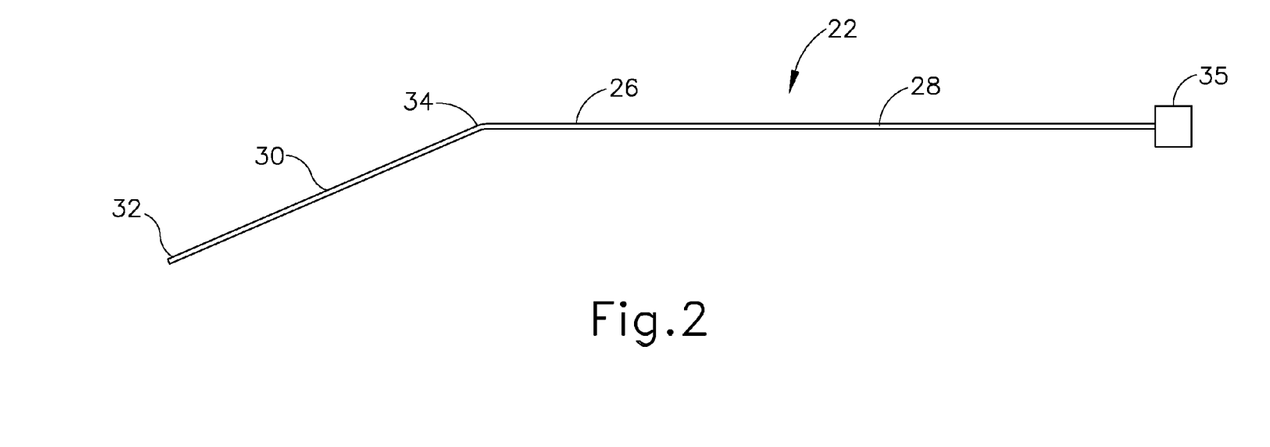
FIG. 2 depicts a side view of the stylet of FIG. 1.

FIG. 2 shows stylet (22) in greater detail. Stylet (22) comprises a core member (26) with a proximal section (28) and a distal section (30). A coil (32) is disposed around at least part of distal section (30) of core member (26). A luer lock member (35) is coupled with a proximal end of core member (26) for coupling with a hub on balloon catheter (10). In some versions, stylet (22) does not include a coil (32). Core member (26) and/or coil (32) may be formed of nitinol, stainless steel, or other biocompatible materials. Distal portion (30) of stylet (22) includes a bend or curve (34) that is stiff enough to bend balloon catheter (10) during the placement of balloon catheter (10) within the airway of the patient. In some versions, stylet (22) may be provided in a generally straight configuration. Stylet (22) may be pre-formed to have a bend (34), or stylet (22) may be malleable, such that a user may bend stylet (22) and stylet (22) maintains the user-created bend. This malleability allows a user to adjust a bend angle according to the airway anatomy of a particular patient. Proximal section (28) of stylet (22) may be generally stiff, a distal section (30) may be generally malleable, and an extreme distal portion may be atraumatic and very flexible or even floppy. This variation in flexibility along the length of stylet (22) may be achieved by using different materials, such as stainless steel and nitinol. Alternatively, one material, such as stainless steel, may be used and the diameter of stylet (22) may be altered to achieve the variation in flexibility along the length of stylet (22).

Stylet (22) has an overall length approximately as long or slightly longer than balloon catheter (10). In some versions, stylet (22) includes an atraumatic, flexible distal tip portion that extends distally out of balloon catheter (10) when stylet (22) is fully disposed within catheter (10). This tip portion may be, for example, between about 0.25 cm to about 8 cm (e.g., about 1-5 cm) in length; and may facilitate the ability of a user to advance system (8) through a patient's airway atraumatically. The overall length of stylet (22) may vary from about 30 cm to about 80 cm, such as from about 45 cm to about 60 cm. Of the overall length, a flexible distal portion of stylet (22) may be from about 5-20 cm, such as from about 10-15 cm. Bend (34) may have any suitable angle, such as from greater than 0 degrees to about 20 degrees. The diameter of stylet (22) may be less than about 1.3 mm, such as 0.9 mm or less. The diameter may decrease distally to about 0.13 mm+/−0.013 mm. Of course, the foregoing dimensions are mere examples. Any other suitable dimensions may be used.

Stylet (22) may be attached to balloon catheter (10), or stylet (22) may be removably connected to balloon catheter (10). Stylet (22) comprises a luer lock member (35) with threads on proximal section (28) that screw into opposing threads disposed on a luer (36) of balloon catheter (10). In some versions, balloon catheter (10) may include a locking mechanism (not shown) to lock stylet (22) in position within catheter (10). The locking mechanism can be any mechanical device, including a lever, a ball and pin, a luer, etc. All or part of distal section (30) of stylet (22) may extend out of the distal end of catheter (10). Stylet (22) may be locked to balloon catheter (10) at different positions or lengths so the distal end of stylet (22) extends out of or is positioned within balloon catheter (10) at different lengths. The length, diameter(s) and stiffness characteristics of stylet (22) may be varied in different embodiments to confer different performance characteristics to the overall system (8).

Use of stylet (22) to insert balloon catheter (10) helps to guide the distal end of balloon catheter (10) through the airway of the patient and to the stenotic region. Stylet (22) provides increased steerability during advancement of balloon catheter (10). Torquability of balloon catheter (10) is also increased when using stylet (22). In some versions, luer lock member (35) of stylet (22) and luer (36) of balloon catheter (10) mate together, so that stylet (22) and balloon catheter (10) may be rotated together and thus steered into a constricted portion of an airway.

In some versions, stylet (22) may have a light emitting portion, such as a light emitting distal end or tip. For example, stylet (22) may include one or more light fibers to transmit light from a light source attached to the proximal end of stylet (22) to its distal end. Light from a light emitting stylet (22) may be used to help a user visualize a patient's airway from the inside using a scope and/or in some cases from the outside via transillumination through the patient's skin. A light emitting guidewire device that may be used or modified to achieve such an illuminating stylet (22) is the Relieva Luma™ Sinus Illumination Guidewire/System, manufactured by Acclarent, Inc. of Menlo Park, Calif. Such an illuminating stylet (22) may have any of the features described above with the additional feature of light emitting capability.

C. Exemplary Method of Use of the System

Figure 3A:
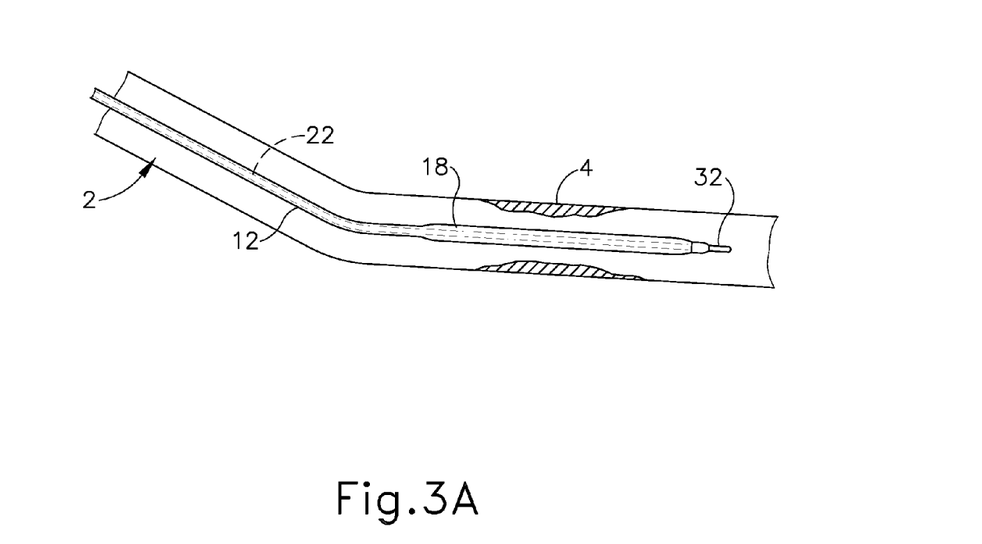
FIG. 3A depicts a cross sectional view of the system of FIG. 1 being introduced into an airway, with the balloon positioned at a stenosis in a collapsed state.
Figure 3B:
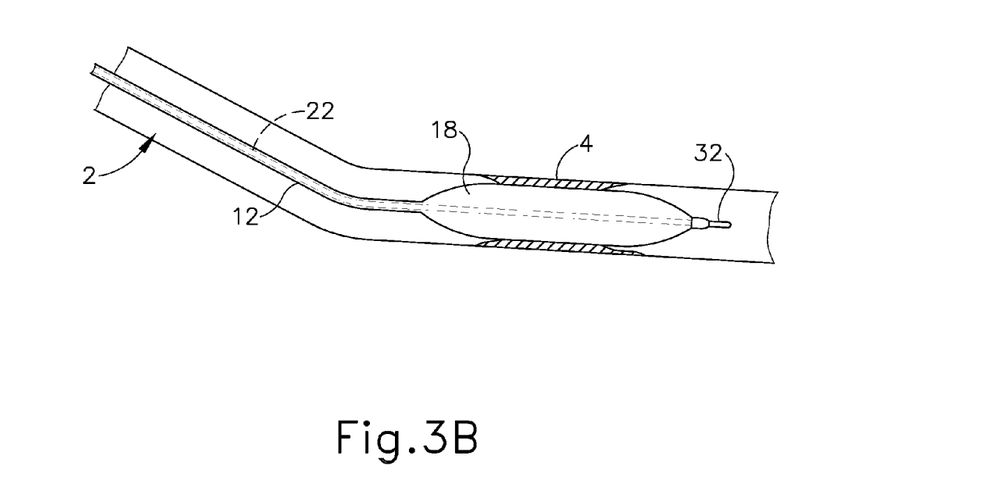
FIG. 3B depicts a cross sectional view of the system of FIG. 3A, with the balloon inflated to a dilated state.

FIGS. 3A and 3B show a method for dilating an stenotic region (4) in an airway (2), such as in a case of subglottic stenosis. Dilation system (8) is introduced through the mouth and into the airway of the patient. Optionally, a bronchoscope (not shown) or other scope device may be used to visualize the positioning of dilation system (8). Dilation system (8) may be bent either by the user or by the manufacturer of system (8). For example, stylet (22) may be bent and then inserted into balloon catheter (10), while in other cases stylet (22) and balloon catheter (10) may be bent together, with stylet (22) already residing in catheter (10). The support of stylet (22) and the bend in the overall system (8) may help a physician navigate system (8) through the patient's airway to position balloon (18) within at least a portion of stenotic region (4). As shown in FIG. 3A, inflatable balloon (18) of the catheter (10) is in an unexpanded configuration during advancement and placement of balloon catheter (10). As shown in FIG. 3B, once balloon (18) is positioned within stenotic region (4) of the airway (2), inflatable balloon (18) is inflated to dilate stenotic region (4). Balloon (18) is then deflated to enable removal from airway (2). By way of example only, balloon (18) may be deflated by actively drawing the fluid from balloon (18); by venting the fluid in balloon (18), allowing the inward pressure imposed by airway (2) to drive fluid from balloon (18); or in any other suitable fashion as will be apparent to those of ordinary skill in the art in view of the teachings herein.

In some versions, stylet (22) remains in balloon catheter (10) during inflation of balloon (18). Maintaining stylet (22) in catheter (10) during inflation may give catheter (10) added column strength and help maintain the position of balloon (18) within stenotic region (4), thus avoiding slipping. In some versions, stylet (22) is removed from balloon catheter (10) before inflating. Stylet (22) may be removed from balloon catheter (10) after balloon catheter (10) is properly positioned within airway (2) of the patient, or stylet (22) can be removed after stenosis (4) has been dilated but before removing balloon catheter (10) from the patient.

Inflatable balloon (18) may be inflated more than once to dilate stenotic region (4) of airway (2). The physician inflates inflatable balloon (18) to a desired pressure during each dilation of stenosis (4). Proper dilation of stenotic region (4) can be confirmed by visualizing the region with the bronchoscope/endoscope.

II. Exemplary Sensing Features in Dilation System

During the inflation of balloon catheter (10), while a user removes the balloon catheter (10) from a passageway in a patient, and/or while the user manipulates the inflated balloon catheter (10), system (8) may provide the ability to monitor the pressures or forces exerted on/within various portions of system (8) such that in the event that excessive force/pressure or excessive change in force/pressure occurs, the user may be alerted and/or system (8) may automatically deflate balloon (18) or otherwise reduce fluid pressure in balloon (18) to avoid risking harm to the patient. Several merely illustrative examples of sensors and associated features will be described in greater detail below; while other examples will be apparent to those of ordinary skill in the art in view of the teachings herein.

A. Exemplary Force Sensor in Dilation System

Figure 4:
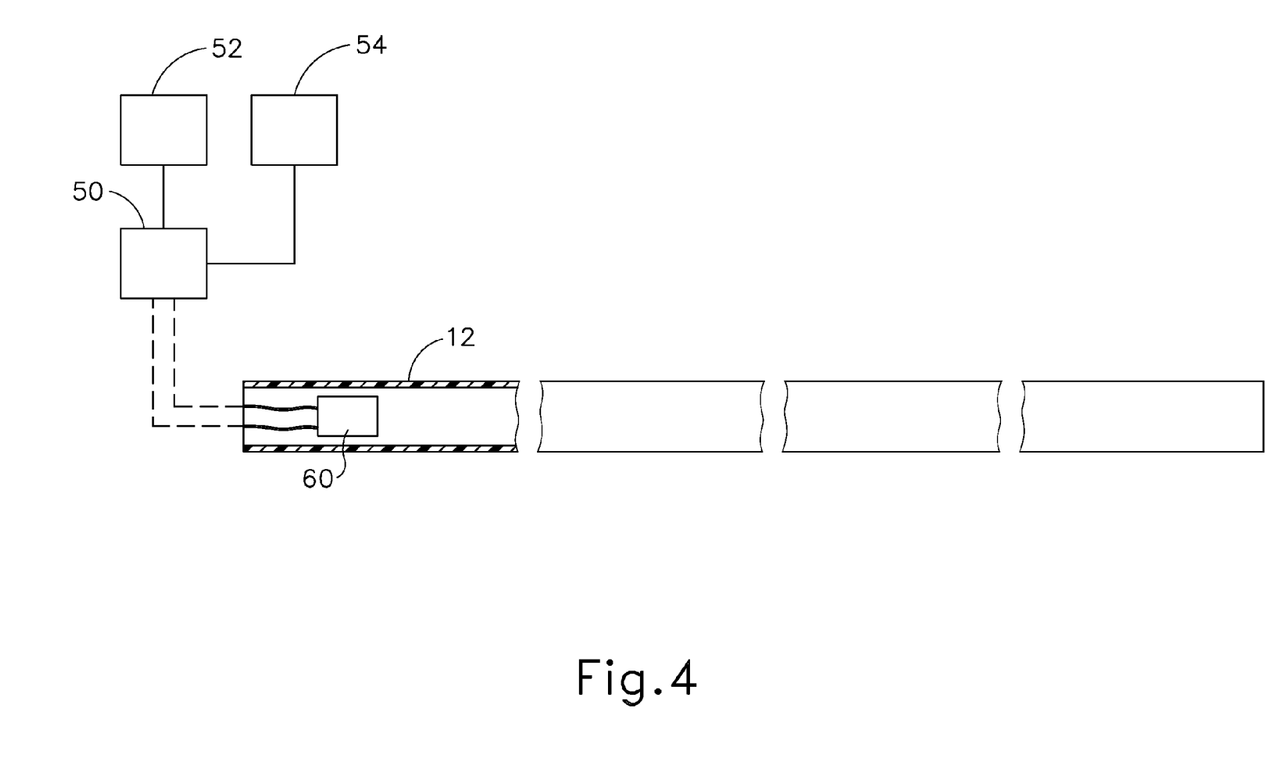
FIG. 4 depicts an enlarged, side view of a portion of the balloon catheter with a force measuring device.

FIG. 4 shows a variation of catheter shaft (12) that includes an integral force sensor (60) in communication with a control module (50). Control module (50) is in communication with a feedback device (52) and a deflation trigger (54). It should be understood that either feedback device (52) and/or deflation trigger (54) may be completely omitted from this combination. In the present example, force sensor (60) is disposed on catheter shaft (12) and is operable to sense force in the form of tensile strain on catheter shaft (12). Thus, in the event that the user attempts to remove inflatable balloon (18) from an anatomical passageway before inflatable balloon (18) is sufficiently deflated, a spike in strain force may occur along catheter shaft (12), and this spike in force may be detected using force sensor (60). Force data from force sensor (60) may be communicated to control module (50), where the force data is processed. In other exemplary versions, force sensor (60) may be positioned on stylet (22) and/or in any other suitable location within system (8) where a spike in strain or other forces may be experienced as a result of a premature attempt to remove inflatable balloon (18) from a patient's airway (40) or other anatomical passageway.

By way of example only, at least part of force sensor (60) could be applied as a decal to the exterior of shaft (12) or as a decal to the interior of shaft (12). In some versions, force sensor (60) has an annular shape and encircles the inner or outer perimeter of shaft (12). In addition or in the alternative, force sensor (60) could be embedded within the sidewall of shaft (12). Force sensor (60) may be positioned near the proximal end of shaft (12), near the distal end of shaft (12), or anywhere in between the proximal and distal ends of shaft (12). It should also be understood that shaft (12) may have a plurality of force sensors (30).

Force sensor (60) is operable to measure the tensile strain on catheter shaft (12). In some versions, force sensor (60) comprises a strain gauge. For instance, force sensor (60) may comprise a pair of spaced-apart conductive members having a voltage applied thereto, such that force sensor (60) defines a capacitance. The spacing of the conductive members may change when catheter shaft (12) deforms (e.g. stretches longitudinally) in response to strain, such that the conductive members may provide a change in capacitance in response to strain-induced deformation of catheter shaft (12). As yet another merely illustrative example, force sensor (60) may include a resistance sensor or piezoelectric sensor. Alternatively, force sensor (60) may include any other suitable type device operable to detect physical strain on catheter shaft (12) as would be apparent to one of ordinary skill in the art in view of the teachings herein.

In addition to or as alternative to detecting strain in catheter shaft (12), force sensor (60) may be operable to detect fluid pressure and/or strain in balloon (18). For instance, force sensor (60) may comprise an inductive coil that is positioned along the surface of inflatable balloon (18) and that is operable to detect sudden or otherwise undesirable changes in strain of the material forming inflatable balloon (18), as a function of changes in the inductance of the inductive coil reflected by movements of the surface of inflatable balloon (18). Other variations of force sensor (60) will be apparent to one of ordinary skill in art in view of the teachings herein.

Control module (50) may comprise a computer, a processor, a simple logic chip, and/or any other suitable component operable to process strain information and/or other force data received from force sensor (60). Control module (50) may further include a memory operable to record information after being measured by force sensor (60). In addition or in the alternative, a memory could store one or more threshold values that a processor could compare against values detected by sensor (60). By way of example only, a force threshold associated with shaft (12) may be anywhere between approximately 7 lbs. and approximately 15 lbs. Other suitable threshold values will be apparent to those of ordinary skill in the art in view of the teachings herein. Similarly, other suitable components that may be incorporated into control module (50) will be apparent to one of ordinary skill in the art in view of the teachings herein.

In the present example, control module (50) is in communication with feedback device (52) and with deflation trigger (54) in the present example, though it should be understood that feedback device (52) and/or deflation trigger (54) may be omitted if desired. Control module (50) may include a control logic that triggers a response (e.g., through feedback device (52), through deflation trigger (54), and/or otherwise) when a force related parameter exceeds a preset threshold value and/or when a rate of change in such a parameter exceeds a threshold value. Suitable threshold values will be apparent to those of ordinary skill in the art in view of the teachings herein. In some instances, the threshold value(s) may be lower than values known to be associated with failure of system (8) and/or injury to the patient. Such threshold values may nevertheless be significantly greater than values associated with expected strain encountered by one or more components of system (8) during normal and proper operation of system (8).

It will be appreciated that, in the event that force detected using force sensor (60) exceeds a certain amount, the user may wish to be notified. Feedback device (52) may thus provide one or more alerts to the user when feedback device (52) is triggered by control module (50) (e.g., when a force related threshold is exceeded as noted above). Feedback device (52) comprises any suitable feedback mechanism operable to inform the user of such an occurrence. For instance, feedback device (52) may include an audio producing feature able to produce a beep, siren, or other suitable noise. In addition to or as an alternative to providing audio feedback, feedback device (52) may include a motor or vibrating element operable to produce haptic feedback for the user to feel. Such haptic feedback may be communicated to a portion of system (8) being gripped by the operator. In some such versions, at least a portion of shaft (12) is isolated to prevent the haptic feedback from reaching the anatomical passageway where balloon (18) is disposed.

In addition to or as an alternative to providing audio feedback and/or haptic feedback, feedback device (52) may provide visual feedback. For instance, feedback device (52) may include a color-changing feature, a flashing light, an LCD screen with gradually increasing bars, a numerical display, and/or any other suitable type of visual indicator operable to inform a user that a particular level of force has been exceeded. In some versions, visual feedback is provided through a feature of shaft (12) or hub (14). In addition or in the alternative, visual feedback may be provided through a separate display. For instance, visual feedback may be provided through a display screen that is used to also display the image from an endoscopic camera viewing the anatomical passageway of the patient, such that the operator will receive the visual feedback while viewing the endoscopic display screen. As yet another merely illustrative variation, visual feedback may be provided through a device that is removably clipped to a display screen that is used to also display the image from an endoscopic camera viewing the anatomical passageway of the patient, again such that the operator will receive the visual feedback while viewing the endoscopic display screen. Still other suitable ways in which feedback device (52) may provide visual feedback will be apparent to those of ordinary skill in the art in view of the teachings herein. It should also be understood that, any combination of audio, visual, and/or haptic feedback may be produced by feedback device (52) in order to inform the user that a particular level of force (or rate of change in force) has been exceeded. Still other suitable forms that feedback device (30) may take will be apparent to those of ordinary skill in the art in view of the teachings herein.

In some versions, it will be understood that control module (50), feedback device (52), and force sensor (60) may be used to detect and inform the user of varying levels of force along catheter shaft (12). For instance, a threshold for a medium level of force may be set in control module (50) with a corresponding feedback signal from feedback device (52) (e.g., an intermittent beep). A different threshold for a high level of force may be set in control module (50) with a corresponding feedback signal from feedback device (52) (e.g., a louder/faster, persistent beep). The user may thus be informed of when a first level of force is being applied to catheter shaft (12) and when a second, perhaps more dangerous level of force is applied to catheter shaft (12).

Deflation trigger (54) may provide deflation of balloon (18) or otherwise reduce fluid pressure in balloon (18) when deflation trigger (54) is triggered by control module (50) (e.g., when a force related threshold is exceeded as noted above). Deflation trigger (54) may comprise any suitable feature(s) operable to cause inflatable balloon (18) to deflate or to otherwise reduce fluid pressure in balloon (18). In the event that a threshold amount (e.g., a critical threshold) is detected to be exceeded by force sensor (60), deflation trigger (54) may trigger saline to be removed from inflatable balloon (18) (e.g., using venting or suction), thereby causing inflatable balloon (18) to immediately deflate. In some versions, deflation trigger (54) may also be operable to actuate a balloon rupturing feature and/or shaft rupturing feature such as one described in U.S. patent application Ser. No. 13/795,857, entitled "Apparatus for Puncturing Balloon in Airway Dilation Shaft," filed on even date herewith, published as U.S. Pub. No. 2014/0277059 on Sep. 18, 2014, the disclosure of which is incorporated by reference herein. Other suitable forms that deflation trigger (54) may take will be apparent to those of ordinary skill in the art in view of the teachings herein. It should also be understood that system (8) may include a feature that is operable to rupture balloon (18) and/or shaft (12), without such a feature necessarily being automatically activated by control module (50). For instance, an operator may manually activate a rupturing feature in response to feedback from feedback device (52) indicating that a force value has exceeded a threshold.

In versions having both feedback device (52) and deflation trigger (54), control module (50) may be configured to first activate feedback device (52) when a sensed force or pressure value exceeds a first threshold value; then activate deflation trigger (54) when a sensed force or pressure value exceeds a second, higher threshold value. Other suitable permutations and operations will be apparent to those of ordinary skill in the art in view of the teachings herein.

B. Exemplary Pressure Sensor in Dilation System

While the examples above relate to strain encountered by catheter shaft (12) when a user attempts to remove inflatable balloon (18) from a stenotic region (46) before inflatable balloon (18) is sufficiently deflated, it should be understood that the fluid pressure within inflatable balloon (18) may also change or spike when a user attempts to remove inflatable balloon (18) from a stenotic region (46) before inflatable balloon (18) is sufficiently deflated. Accordingly, the user may wish to monitor the fluid pressure within inflatable balloon (18) in addition to or in lieu of monitoring the strain on catheter shaft (12).

Figure 5:
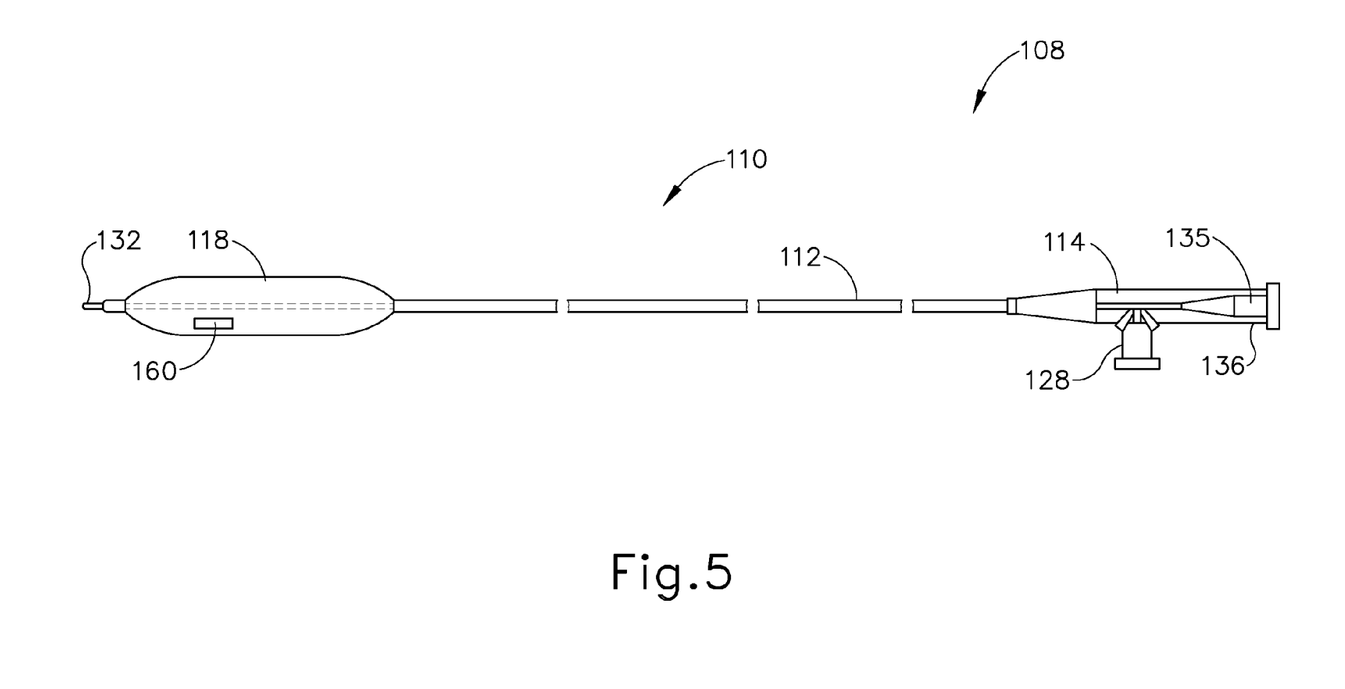
FIG. 5 depicts an alternative exemplary version of a system for dilating a stenosis with a strain gauge positioned near a balloon of the balloon catheter and without a stylet.

FIG. 5 shows an exemplary system (108) for dilating a stenotic region (46) of an airway (40). System (108) comprises a balloon catheter (110) and an inflatable balloon (118), similar to catheter (10) and balloon (18) described above. Inflatable balloon (118) terminates in a distal tip (132). Balloon catheter (110) comprises a catheter shaft (112) leading to a proximal section (114). Proximal section (114) comprises an inflation port (128) and luer (136) with a corresponding luer lock (135) feature. It will be appreciated that the aforementioned components are substantially similar to the similarly named components with respect to system (8) shown in FIG. 1. System (108) differs in that a stylet such as stylet (22) of FIG. 1 has been omitted from the view shown in FIG. 5, though it should be understood that a stylet (22) may be used with system (108). Furthermore, a pressure sensor (160) has been positioned within inflatable balloon (118). It should be understood that pressure sensor (160) may be located elsewhere (e.g., within a lumen of shaft (112) that is in fluid communication with inflatable balloon (118)). Pressure sensor (160) may comprise a strain gauge and/or any other suitable type of sensor that is sensitive to the pressure of fluid within balloon (118).

Pressure sensor (160) is further in communication with a control module (50), feedback device (52), and deflation trigger (54), in a manner similar to the arrangement described above with reference to FIG. 4. As a result, as system (108) is being used, pressure readings from pressure sensor (160) are continually monitored by control module (50). In the event that the fluid pressure within inflatable balloon (118) exceeds a threshold pressure, or when the fluid pressure changes at a rate that exceeds a threshold, control module (50) may send instructions for feedback device (52) to alert the user. In addition or in the alternative, deflation deflation trigger (54) may trigger removal of saline from inflatable balloon (118) (e.g., using venting, suction, etc.), thereby causing inflatable balloon (118) to immediately deflate or otherwise lose fluid pressure. In some versions, deflation trigger (54) may also be operable to actuate a balloon rupturing feature and/or shaft rupturing feature such as one described in U.S. patent application Ser. No. 13/795,857, entitled "Apparatus for Puncturing Balloon in Airway Dilation Shaft," filed on even date herewith, published as U.S. Pub. No. 2014/0277059 on Sep. 18, 2014, the disclosure of which is incorporated by reference herein. Other suitable forms that deflation trigger (54) may take will be apparent to those of ordinary skill in the art in view of the teachings herein.

In any of the foregoing examples, control module (50) may include a reset feature that enables balloon (18, 118) to be re-inflated if the value detected by sensor (60, 160) falls below a threshold and the integrity of balloon (18, 118) has not been compromised (e.g., balloon (18, 118) was not ruptured in response to a pressure exceeding a threshold, etc.). For instance, a reset button or other reset feature may be manually actuated by the operator. Alternatively, a system reset may be automated such that control module (50) resets automatically once a value detected by sensor (60, 160) falls below a threshold.

III. Miscellaneous

It should be understood that any of the versions of system described herein may include various other features in addition to or in lieu of those described above. By way of example only, any of the devices herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:
1. An apparatus comprising:
    (a) a balloon catheter defining a lumen operable to communicate fluid;
    (b) an inflatable balloon disposed on the distal end of the balloon catheter, wherein the inflatable balloon is in fluid communication with the lumen, wherein the inflatable balloon is positionable within a passageway within a patient;
    (c) a force sensor associated with one or both of the balloon catheter or the inflatable balloon, wherein the force sensor is configured to sense force associated one or both of the balloon catheter or the inflatable balloon;
    (d) a balloon pressure reduction feature operable to reduce fluid pressure in the balloon; and
    (e) a control module in communication with the balloon pressure reduction feature, wherein the control module is further in communication with the force sensor, wherein the control module is configured to receive force data from the force sensor and compare the force data to a predetermined threshold value.

2. The apparatus of claim 1, wherein the force sensor comprises a strain gauge.

3. The apparatus of claim 1, wherein the force sensor is located within the inflatable balloon.

4. The apparatus of claim 3, wherein the force sensor comprises a pressure gauge operable to measure changes in the pressure within the inflatable balloon.

5. The apparatus of claim 1, further comprising a user feedback feature in communication with the control module, wherein the user feedback feature is operable to provide a perceivable feedback to a user indicating that a threshold value has been exceeded by force data from the force sensor.

6. The apparatus of claim 5, wherein the perceivable feedback comprises an auditory feedback.

7. The apparatus of claim 5, wherein the perceivable feedback comprises a haptic feedback.

8. The apparatus of claim 5, wherein the perceivable feedback comprises a visual feedback.

9. The apparatus of claim 1, wherein the inflatable balloon has an elongated generally cylindrical shape.

10. The apparatus of claim 1, further comprising a stylet operable to fit within the balloon catheter, wherein the stylet is configured to guide the inflatable balloon through an airway.

11. The apparatus of claim 1, wherein the passageway comprises an airway.

12. An apparatus comprising:
    (a) a balloon catheter defining a lumen operable to communicate fluid, wherein the balloon catheter comprises a shaft;
    (b) an inflatable balloon disposed on the shaft of the balloon catheter, wherein the inflatable balloon is in fluid communication with the lumen, wherein the inflatable balloon is positionable within a passageway within a patient; and
    (c) a force sensor associated with one or both of the balloon catheter or the inflatable balloon, wherein the force sensor is configured to sense force associated one or both of the balloon catheter or the inflatable balloon, wherein the force sensor comprises a strain gauge, wherein the strain gauge is configured to sense tensile strain on the shaft; further comprising a control module, wherein the force sensor is in communication with the control module, wherein the control module is configured to receive force data from the force sensor; wherein the control module is configured to activate the force sensor to reduce pressure in the balloon in response to a threshold value being exceeded by force data from the force sensor.

13. An apparatus comprising:
(a) a balloon catheter defining a lumen operable to communicate fluid, wherein the balloon catheter comprises a shaft;
(b) an inflatable balloon disposed on the shaft of the balloon catheter, wherein the inflatable balloon is in fluid communication with the lumen, wherein the inflatable balloon is positionable within a passageway within a patient; and
(c) a force sensor associated with one or both of the balloon catheter or the inflatable balloon, wherein the force sensor is configured to sense force associated one or both of the balloon catheter or the inflatable balloon, wherein the force sensor is configured to measure a characteristic of the shaft; further comprising a control module, wherein the force sensor is in communication with the control module, wherein the control module is configured to receive force data from the force sensor; wherein the control module is configured to activate the force sensor to reduce pressure in the balloon in response to a threshold value being exceeded by force data from the force sensor.

\* \* \* \* \*